(12) United States Patent
Zimmerman

(10) Patent No.: US 11,439,841 B2
(45) Date of Patent: Sep. 13, 2022

(54) METHODS AND DEVICES FOR TREATMENT OF SUBCUTANEOUS FAT

(71) Applicant: LIGHTFECTIVE LTD., Caesarea (IL)

(72) Inventor: Yotam Zimmerman, Hadera (IL)

(73) Assignee: LIGHTFECTIVE LTD, Caesarea (IL)

( * ) Notice: Subject to any disclaimer, the term of this patent is extended or adjusted under 35 U.S.C. 154(b) by 498 days.

(21) Appl. No.: 16/608,848

(22) PCT Filed: May 1, 2018

(86) PCT No.: PCT/IL2018/050482
§ 371 (c)(1),
(2) Date: Oct. 27, 2019

(87) PCT Pub. No.: WO2018/211492
PCT Pub. Date: Nov. 22, 2018

(65) Prior Publication Data
US 2020/0197723 A1 Jun. 25, 2020

Related U.S. Application Data

(60) Provisional application No. 62/507,806, filed on May 18, 2017.

(51) Int. Cl.
*A61N 5/06* (2006.01)
*A61N 5/00* (2006.01)

(52) U.S. Cl.
CPC ...... *A61N 5/0625* (2013.01); *A61N 2005/005* (2013.01); *A61N 2005/007* (2013.01); *A61N 2005/0632* (2013.01); *A61N 2005/0643* (2013.01); *A61N 2005/0652* (2013.01); *A61N 2005/0659* (2013.01)

(58) Field of Classification Search
CPC ............ A61N 5/0625; A61N 2005/007; A61N 2005/0643; A61N 2005/0652; A61N 2005/0659; A61N 5/0616; A61N 2005/005; A61N 2005/0632; A61N 5/06–2005/073; A61B 18/203; A61B 2018/00005; A61B 2018/00464; A61H 15/02; A61H 2201/0207; A61H 2201/0214; A61H 2207/00; A61H 7/005; A61H 9/0057; A61F 7/00–2007/126
See application file for complete search history.

(56) References Cited

U.S. PATENT DOCUMENTS

| 6,086,247 | A | 7/2000 | von Hollen |
| 6,354,297 | B1 | 3/2002 | Eiseman |
| 6,551,234 | B1 * | 4/2003 | Martello .................. A61N 2/06 600/15 |
| 6,645,162 | B2 | 11/2003 | Friedman et al. |
| 6,673,096 | B2 | 1/2004 | Lach |

(Continued)

OTHER PUBLICATIONS

International Search Report for PCT/IL2018/050482—dated Aug. 31, 2018.

(Continued)

*Primary Examiner* — Jonathan T Kuo
(74) *Attorney, Agent, or Firm* — Katterle Nupp LLC; Paul Katterle; Robert Nupp

(57) ABSTRACT

Disclosed are methods and devices suitable for transdermally killing adipocytes in a subcutaneous fat layer of a human subject.

19 Claims, 3 Drawing Sheets

(56) References Cited

U.S. PATENT DOCUMENTS

| | | | | |
|---|---|---|---|---|
| 7,351,252 B2* | 4/2008 | Altshuler | ............ | A61B 18/203 606/9 |
| 7,921,853 B2* | 4/2011 | Fiset | .................... | A61N 5/0617 607/94 |
| 8,160,691 B2 | 4/2012 | Jang et al. | | |
| 9,403,028 B2* | 8/2016 | Greff | ........................ | A61N 2/00 |
| 10,765,880 B2* | 9/2020 | Sokolowski | ........... | A61N 2/006 |
| 2003/0069618 A1* | 4/2003 | Smith, III | .............. | A61Q 19/06 607/91 |
| 2004/0093042 A1* | 5/2004 | Altshuler | ............. | A61B 18/203 607/88 |
| 2006/0287696 A1 | 12/2006 | Wright et al. | | |
| 2007/0129711 A1 | 6/2007 | Altshuler et al. | | |
| 2007/0179482 A1* | 8/2007 | Anderson | ............ | A61B 18/203 606/2 |
| 2007/0198004 A1* | 8/2007 | Altshuler | ............. | A61N 5/0616 606/9 |
| 2007/0276455 A1* | 11/2007 | Fiset | ...................... | B82Y 30/00 607/91 |
| 2008/0262394 A1 | 10/2008 | Pryor et al. | | |
| 2008/0262574 A1 | 10/2008 | Briefs et al. | | |
| 2012/0109241 A1* | 5/2012 | Rauscher | ............... | A61N 1/326 607/45 |
| 2013/0116758 A1 | 5/2013 | Levinson et al. | | |
| 2013/0123765 A1 | 5/2013 | Zarsky et al. | | |
| 2013/0331637 A1* | 12/2013 | Greff | ........................ | A61N 2/00 600/15 |
| 2014/0081359 A1* | 3/2014 | Sand | .................... | A61N 5/0613 607/90 |
| 2016/0089202 A1 | 3/2016 | Schomacker et al. | | |
| 2017/0106201 A1* | 4/2017 | Schwarz | .............. | A61N 5/0625 |
| 2017/0304646 A1 | 10/2017 | Pryor et al. | | |
| 2018/0271597 A1 | 9/2018 | Eisenmann et al. | | |
| 2018/0303406 A1 | 10/2018 | McKinney et al. | | |

OTHER PUBLICATIONS

Written Opinion of the ISA for PCT/IL2018/050482—dated Aug. 31, 2018.

* cited by examiner

METHODS AND DEVICES FOR TREATMENT OF SUBCUTANEOUS FAT

CROSS-REFERENCE TO RELATED APPLICATIONS

This application is the U.S. national phase of PCT Application No. PCT/IL2018/050482 filed on May 1, 2018, which claims priority to U.S. Provisional Patent Application No. 62/507,806 filed on May 18, 2017, the disclosures of which are incorporated in their entirety by reference herein.

FIELD AND BACKGROUND OF THE INVENTION

The invention, in some embodiments, relates to the field of subcutaneous fat, and in some embodiments to non-surgical, non-invasive, cosmetic treatments for changing the aesthetic appearance of a portion of a human body by killing subcutaneous adipocytes, as well as devices suitable for killing subcutaneous adipocytes.

There is a demand for changing the aesthetic appearance of a portion of a human body, for example by the removal of subcutaneous fat from portions of the body.

One method of removing subcutaneous fat is by killing adipocytes in the subcutaneous layer, for example, by maintaining the cells at a temperature of above 42° C. (typically 42° C. to 47° C.) for a period of time to initiate apoptosis of the adipocytes.

A challenge is to heat the adipocytes to the required temperatures to kill the adipocytes, while maintaining the temperature of the epidermis and dermis below 42° C. to avoid heat damage to the skin. Radiofrequency heating is insufficient due to the low electrical conductivity of fat. Ultrasound heating is considered dangerous due to the possibility that the ultrasound energy will penetrate too deeply into the body of the subject to damage tissue below the subcutaneous layer. Devices (e.g., SculpSure by Cynosure Inc., Westford, Mass., USA) that use beams of near-infrared laser light having wavelengths of 1060 nm. Such laser light is minimally absorbed by the skin so passes through the skin without substantial attenuation to be effectively absorbed by the adipocytes, thereby transdermally heating the subcutaneous layer adipocytes without damaging skin. Due to the power density of the laser beam, adipocytes within the laser beam are quickly heated to a degree that initiates apoptosis. Due to relatively large area that needs to be treated the laser power required is high (in scale of tens of watts) and such devices are very expensive.

Non-invasive methods for changing the aesthetic appearance of a portion of a human body are sought after.

SUMMARY OF THE INVENTION

Some embodiments of the invention relate to changing the aesthetic appearance of a portion of a human body by killing subcutaneous adipocytes as well as devices suitable for killing subcutaneous adipocytes. In some embodiments, the methods are non-surgical, non-invasive, cosmetic treatments for changing the aesthetic appearance of a portion of a human body.

Aspects and embodiments of the invention are described in the specification herein below and in the appended claims.

Unless otherwise defined, all technical and scientific terms used herein have the same meaning as commonly understood by one of ordinary skill in the art to which the invention pertains. In case of conflict, the specification, including definitions, will take precedence.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

As used herein, the indefinite articles "a" and "an" mean "at least one" or "one or more" unless the context clearly dictates otherwise.

As used herein, when a numerical value is preceded by the term "about", the term "about" is intended to indicate +/−10%.

BRIEF DESCRIPTION OF THE FIGURES

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale. In the Figures.

DESCRIPTION OF SOME EMBODIMENTS OF THE INVENTION

Figure 1:
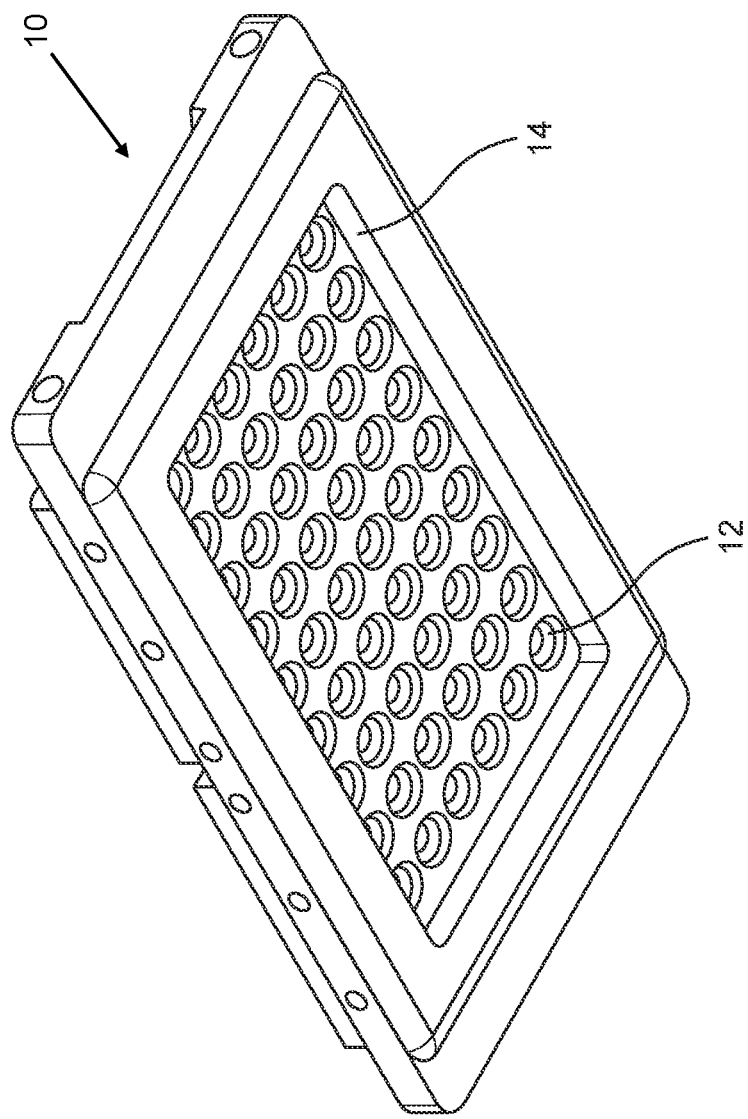
FIG. 1 depicts a panel of LEDs suitable for implementing some embodiments of the teachings herein.

Some embodiments of the invention relate to changing the aesthetic appearance of a portion of a human body by killing subcutaneous adipocytes as well as devices suitable for killing subcutaneous adipocytes. In some embodiments, the methods are non-surgical, non-invasive, cosmetic treatments for changing the aesthetic appearance of a portion of a human body.

Before explaining at least one embodiment in detail, it is to be understood that the invention is not necessarily limited in its application to the details of construction and the arrangement of the components and/or methods set forth herein. The invention is capable of other embodiments or of being practiced or carried out in various ways. The phraseology and terminology employed herein are for descriptive purpose and should not be regarded as limiting.

As discussed in the background section above, there is a demand for changing the aesthetic appearance of a portion of a human body. Embodiments of the teachings herein relate to non-surgical non-invasive cosmetic methods for changing the aesthetic appearance of a portion of a human body.

The teachings herein are based on the discovery that adipocytes in a subcutaneous fat layer of a human can be transdermally killed with few side effects by heating the subcutaneous fat layer with near-infrared light having wavelengths in a range of between 850 nm and 1100 nm.

Without wishing to be held to any one theory, it is currently believed that a illumination light that consists essentially of the above-recited near-infrared range of wavelengths are not substantially absorbed by skin and therefore effectively passes through the epidermis and dermis with sufficient intensity to be absorbed by and heat adipocytes to a temperature of above 42° C. (typically 42° C. to 47° C.) for a duration sufficient to initiate apoptosis and thereby kill at least some of the adipocytes.

It has also been found that at the duration and intensities of light in the recited wavelength near-infrared range required for killing the adipocytes in the subcutaneous layer, the light is sufficiently absorbed by collagen in the subcutaneous layer to stimulate collagenesis without damaging the collagen. This serendipitously leads to transdermal heating according to the teachings herein providing a skin-tightening effect concurrently with the adipocyte-killing effect, thereby providing an improved aesthetic appearance of a portion of a human body that is sculpted by the killing of the adipocytes with a lesser incidence of saggy skin.

In order to avoid damaging the epidermis by burning, it is typically necessary to maintain the temperature of the portion of the epidermis through which the illumination light passes to below 42° C. It has been found that at the duration and intensities of light in the recited wavelength near-infrared range required for killing the adipocytes in the subcutaneous layer the dermis and epidermis are not substantially damaged if the epidermis is sufficiently cooled.

Methods for Changing the Appearance of a Portion of a Human Body

Thus according to an aspect of some embodiments of the teachings herein, there is provided a non-surgical, non-invasive cosmetic method for changing the aesthetic appearance of a portion of a human body by killing subcutaneous adipocytes, comprising:
  a. through a portion of the epidermis of a human subject, transdermally heating a portion of a subcutaneous fat layer of the subject with incoherent multi-source illumination light, the illumination light having a cross sectional area at the surface of the epidermis with dimensions sufficiently bigger than thickness of the skin thickness, the heating sufficient to kill at least some adipocytes in the portion of the subcutaneous fat layer and/or to initiate apoptosis thereof; and
  b. concurrently with the transdermal heating, cooling the portion of epidermis sufficiently to prevent burn damage to the epidermis,
wherein the illumination light consists essentially of light having wavelengths in a near-infrared range of not less than 850 nm and not more than 1100 nm,
thereby destroying adipocytes in the portion of the subcutaneous fat layer.

According to an aspect of some embodiments of the teachings herein, there is also provided a method for changing the appearance of a portion of a human body by killing subcutaneous adipocytes, comprising:
  a. through a portion of the epidermis of a human subject, transdermally heating a portion of a subcutaneous fat layer of the subject with incoherent multi-source illumination light, the illumination light having a cross sectional area at the surface of the epidermis with dimensions sufficiently bigger than thickness of the skin thickness, the heating sufficient to kill at least some adipocytes in the portion of the subcutaneous fat layer; and
  b. concurrently with the transdermal heating, cooling the portion of epidermis sufficiently to prevent burn damage to the epidermis,
wherein the beam consists essentially of light having wavelengths in a near-infrared range of not less than 850 nm and not more than 1100 nm,
thereby destroying adipocytes in the portion of the subcutaneous fat layer.

In some embodiments, the total power density of the recited wavelengths of the illumination light in the near-infrared range is not less than 0.3 W/cm$^2$ and not more than 5 W/cm$^2$.

In some embodiments, the transdermal heating of the subcutaneous fat layer of the subject is performed during at least one session, wherein each volume of treated subcutaneous fat layer is continuously transdermally heated for a duration of at least 10 minutes.

As noted above, the illumination light is incoherent multi-source illumination light. In some embodiments, the light is generated by at matrix of high-power light-emitting diodes.

In some embodiments, the cooling comprises contacting the portion of epidermis with a cooling surface of a physical component, the surface having a temperature of between 5° C. and 20° C. In some embodiments, the cooling surface is the surface of an optical element through which the illumination light passes.

In some embodiments, the method further comprises: concurrently with the transdermal heating, applying suction to the portion of epidermis thereby drawing tissue including the portion of epidermis into an irradiation enclosure. In some embodiments, such drawing of tissue into a radiation enclosure localizes the epidermis in a specified location for better cooling and/or localizes the subcutaneous fat for better heating by the illumination light.

In some embodiments, the method further comprises: concurrently with the transdermal heating, mechanically drawing tissue including the portion of epidermis into an irradiation enclosure. In some embodiments, such drawing of tissue localizes the epidermis in a specified location for better cooling and/or localizes the subcutaneous fat for better heating by the illumination light.

In some embodiments, the drawing of the tissue is such that the portion of the subcutaneous fat layer of the subject to be heated is located inside the irradiation enclosure; and the illumination light is projected across the irradiation enclosure so that at least some of the illumination light travels in a direction that passes through the portion of epidermis, through the portion of the subcutaneous fat layer and out through an opposing portion of epidermis.

In some embodiments, concurrently with the transdermal heating, the method further comprises applying a pulsed electromagnetic field to the volume of tissue that includes the portion of epidermis, the underlying dermis and the portion of the subcutaneous fat layer. In some embodiments, the pulsed electromagnetic field has a field strength of not less than 10 Gauss and not more than 30 Gauss and has a magnetic pulse frequency of not less than 0.1 Hz and not more than 100 Hz. It has been found that concurrent application of a pulsed electromagnetic field leads to advantageous results. Without wishing to be held to any one theory, it is currently believed that such concurrent application of the pulsed electromagnetic field leads to quicker clearance of adipocyte debris and/or stimulates quicker collagenesis. A pulsed electromagnetic field may be applied using any suitable device, for example, a pulsed electromagnetic field generated by a commercially-available pulsed electromagnetic field therapy (PEMFT) device.

In some embodiments, the method further comprises, during the transdermal heating determining a temperature of the portion of the subcutaneous fat layer; and:

if the determined temperature is higher than a predetermined maximum temperature, reducing the intensity of the illumination light; and if the determined temperature is lower than a predetermined minimum temperature, increasing the intensity of the illumination light.

The methods according to the teachings herein may be implemented using any suitable device or combination of devices. Some embodiments are preferably implemented using a device according to the teachings herein.

Device According to the Teachings Herein

According to an aspect of some embodiments of the teachings herein, there is also provided a device suitable for transdermally killing adipocytes in a subcutaneous fat layer of a human subject, comprising:

a. a contact surface having an area of not less than 0.5 cm$^2$ configured for contact with a human skin surface;

b. an illumination unit configured to generate and project illumination light comprising a plurality of near-infrared light-emitting diodes (LEDs) each capable of emitting at least of 0.5 W power, the illumination light having a cross sectional area of not less than 0.5 cm$^2$, the illumination light consisting essentially of non-coherent light having near-infrared wavelengths in a range of not less than 850 nm and not more than 1100 nm, and the illumination light having an intensity sufficient to kill at least some adipocytes in a human subcutaneous fat layer when projected through a human epidermis; and c. a cooling unit configured to cool tissue located in a volume in proximity to the contact surface and through which the illumination light passes, the cooling unit having a cooling capacity of at least 0.3 W/cm2

In some embodiments, the illumination unit is configured so that the illumination light has a total power density of the recited wavelengths in the near-infrared range of not less than 0.3 W/cm$^2$ and not more than 5 W/cm$^2$.

In some embodiments, the LEDs are arranged on a supporting structure at a density of 0.25-4 LEDs per cm$^2$.

In some preferred embodiments, the illumination unit comprises: a matrix of said near-infrared LEDs separated by a distance of not less than 0.5 cm and not more than 2 cm; and the contact surface if of a high thermal conductivity material (e.g., sapphire); and the cooling unit comprises cooling blocks located between rows of the LEDs.

In some embodiments, the illumination unit is configured for generating the illumination light continuously for a duration of not less than 10 minutes.

In some embodiments, the cooling unit is configured to maintain the temperature of the contact surface at a temperature of between 5° C. and 20° C. In some embodiments, the contact surface is the surface of a transparent element through which the illumination light passes.

In some embodiments, the device further comprises a cooling block;

the cooling unit is configured to maintain the temperature of the cooling block at a temperature of less than 20° C.; and the device is configured so that during use of the device when the contact surface contacts a skin surface, the cooling block contacts the skin surface to absorb heat from the skin surface.

In some embodiments, the cooling unit comprises at least one cooling block, each cooling block located between a row of the LEDs.

In some embodiments, the cooling block constitutes a portion of an irradiation enclosure having a rim; and the illumination unit is configured to project the illumination light into the irradiation enclosure towards a plane defined by the rim.

In some embodiments, the device further comprises an irradiation enclosure with a sealing rim; and a suction generator, configured to draw air from inside the radiation enclosure. In some embodiments, the illumination unit is configured to project the illumination light into the irradiation enclosure towards a plane defined by the sealing rim.

In some embodiments, the radiation enclosure comprises a window transparent to the illumination light; and the illumination unit is configured to project the illumination light into the irradiation enclosure towards a plane defined by the sealing rim through the window.

In some embodiments, the device comprises a window positioned at least at two opposite sides of the radiation enclosure; wherein the angle between the two opposite sides is not more than 90°. In some embodiments, the angle between the two opposite sides is not more than 60°. In some embodiments, the angle between the two opposite sides is not more than 30°.

In some embodiments, the device further comprises: a pulsed electromagnetic field generator, configured to generate a pulsed electromagnetic field in a volume that includes a illumination light projected by the illumination unit in proximity of the contact surface. In some embodiments, the pulsed electromagnetic field generator is configured to generate a pulsed electromagnetic field having a field strength of between 10 Gauss and 30 Gauss with a magnetic pulse frequency of between 0.1 Hz and 100 Hz. In some embodiments, the pulsed electromagnetic field generator comprises a coil with ferromagnetic core for generating the pulsed electromagnetic field.

Wavelengths for Implementing the Teachings Herein

As noted above, methods according to the teachings herein include transdermally heating a portion of a subcutaneous fat layer of the subject with a illumination light wherein the illumination light consists essentially of light having wavelengths in a near-infrared range of not less than 850 nm and not more than 1100 nm, thereby destroying adipocytes in the portion of the subcutaneous fat layer, and as noted above, serendipitously stimulating collagenesis in the subcutaneous layer while not damaging the dermis.

The wavelength may be chosen according to penetration depth required.

Accordingly, devices according to the teachings herein include an illumination unit configured to generate and project a illumination light, the illumination light consisting essentially of light having wavelengths in a near-infrared range of not less than 850 nm and not more than 1100 nm.

Preferably the wavelengths are in a near-infrared range selected from the group of ranges consisting of 900 nm to 920 nm; 940 nm to 960 nm; and 1010 nm to 1100 nm. In some preferred embodiments, the range is 940 nm to 960 nm. It has been found that in the more preferred ranges, the adipocyte killing effect and the collagenesis stimulating effect are improved As used herein, the term "illumination light consisting essentially of light having wavelengths in a near-infrared range" relates to the total intensity of near-infrared light having wavelengths in the recited range of the illumination light compared to the total intensity of all near-infrared light (750 nm to 1400 nm) of the illumination light, in some embodiments being not less than 50%, not less than 80% and even not less than 90% of the total intensity of all near-infrared light. Such preference for light having wavelengths in the recited near-infrared range is to ensure that the desired physiological effects are achieved without damaging tissue by irradiation with wavelengths of near-infrared light that are lower or higher than those in the recited range.

In FIG. 1 is depicted a non-limiting example of panel 10 useful as a component of an illumination unit of a device according to the teachings herein. Panel 10 includes fifty-six individual LEDs 12, centroid wavelength 940 nm, at FWHM 930 nm-965 nm) arranged in a 7×8 matrix that, when activated produce light that passes through a rectangular 5 cm×7 cm cooled sapphire window 14 as a illumination light having cross sectional area of 35 cm². Panel 10 is configured to allow activation of each LED 12 individually, alone or together with any other number of the other fifty-five LEDs 12. As each LED 12 is capable of emitting 1000 mW of near-infrared light, panel 10 is able to produce a illumination light having cross sectional area of 35 cm². with a power density of 1.6 W/cm².

Figure 2:
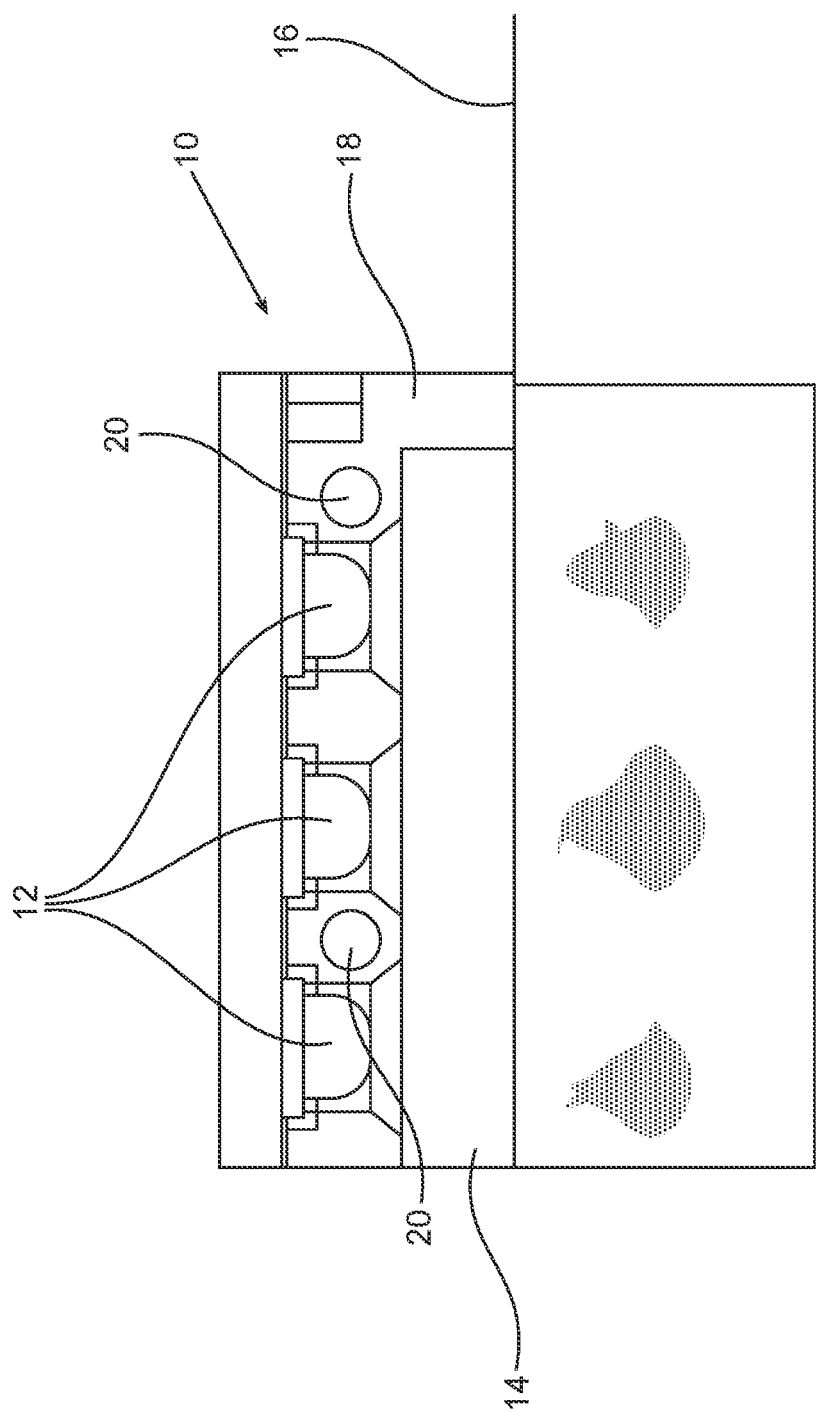
FIG. 2 depicts a portion of the panel of FIG. 1 being used to treat tissue, showing the distribution of light energy inside the treated tissue in side cross section.

In FIG. 2, panel 10 is depicted in partial side cross section (only three LEDs 12 of a row of seven are depicted) where sapphire window 14 acting as a contact surface is in contact with epidermis 16 of a subject. Apparent in FIG. 2 is aluminum frame 18 through which coolant conduits 20 (in cross section) pass, configured to transport a cooling-liquid such as water to cool LEDs 12 and window 14 during operation of a device comprising panel 10. Underneath epidermis 16, shades of gray qualitatively depict the temperature of tissue heated by the illumination light produced by panel 10.

Figure 3:
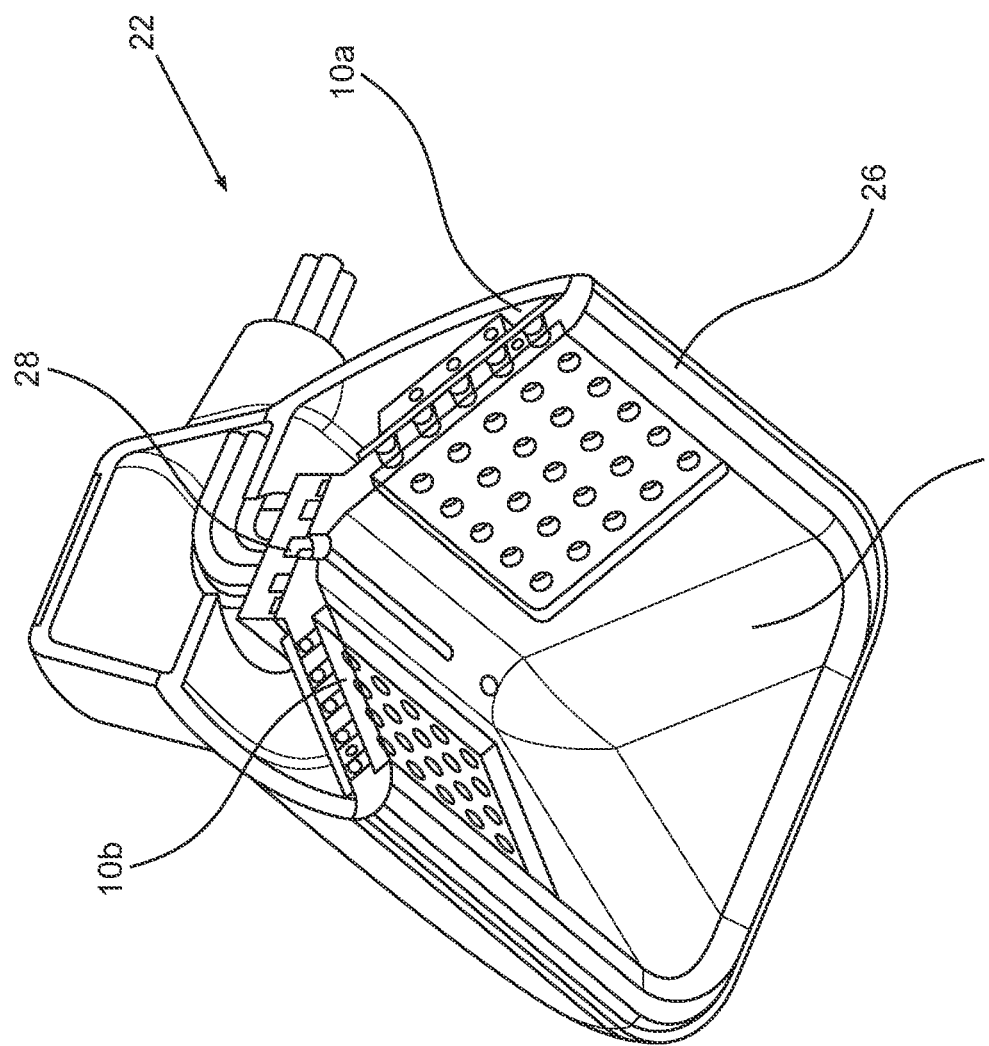
FIG. 3 depicts a portion of a device including an irradiation enclosure according to the teachings herein.

In FIG. 3, a portion of device 22 according to the teachings herein is depicted in partial cut-out, comprising two panels 10a and 10b as described above arranged at 90° one from the other, partially defining an irradiation enclosure 24 including a silicone rubber sealing rim 26 that constitutes a contact surface of device 20. Also seen is suction system 28 configured to draw air from out irradiation enclosure 24. During use of device 22, sealing rim 26 is placed in contact with a portion of epidermis of a subject and suction system 28 activated, while LEDs 12 of panels 10a and 10b are activated. to generate and project a illumination light according to the teachings herein. The suction produced by suction system 28 draws tissue into irradiation enclosure 24.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and scope of the appended claims.

Citation or identification of any reference in this application shall not be construed as an admission that such reference is available as prior art to the invention.

Section headings are used herein to ease understanding of the specification and should not be construed as necessarily limiting.

The invention claimed is:

1. A skin illumination device for treating subcutaneous fat of a subject, comprising:
   a panel that comprises:
      a plurality of LEDs operable to generate light in a near-infrared range to transdermally heat subcutaneous fat of the subject, the LEDs being arranged in a matrix with rows;
      a substrate for positioning proximate to epidermis of the subject, the substrate being transparent to permit light from the LEDs to pass through;
      a frame to which the LEDs and the substrate are mounted, the frame having a plurality of coolant conduits located between the rows of the LEDs, the coolant conduits being configured to transport a cooling-liquid to cool the LEDs and the substrate;
   a generator configured to generate a pulsed electromagnetic field having a field strength of between 10 Gauss and 30 Gauss and a frequency of between 0.1 Hz and 100 Hz; and
   wherein each LED is individually activatable and is operable to be activated alone or together with all or a portion of the other LEDs.

2. The skin illumination device of claim 1, wherein separation between the LEDs in the matrix of LEDs is 0.5 cm to 2 cm.

3. The skin illumination device of claim 1, wherein each LED emits 1000 mW of near-infrared light.

4. The skin illumination device of claim 1, wherein the panel is configured to produce an illumination light with a cross-sectional area of 35 cm².

5. The skin illumination device of claim 1, wherein the panel is configured to produce an illumination light, with a power density of 1.6 W/cm², and wherein an intensity of illumination that passes through epidermis and dermis is sufficient to heat adipocytes to a temperature of above 42° C.

6. The skin illumination device of claim 1, wherein the substrate is a sapphire window, wherein one surface of the sapphire window is configured to contact the frame with the coolant conduits, and another surface of the sapphire window is configured to contact epidermis of the subject.

7. The skin illumination device of claim 1, wherein the frame is comprised of aluminum, and wherein the coolant conduits are configured to transport a cooling-liquid with a cooling capacity of at least 0.3 W/cm2.

8. The skin illumination device of claim 1, wherein the panel is a first panel and wherein the skin illumination device further comprises a second panel comprising a second substrate and plurality of second LEDs mounted to a second frame, the second LEDs being operable to generate light in a near-infrared range to transdermally heat subcutaneous fat of the subject; and
   wherein the first and second panels are oriented at an angle to each other and form an irradiation enclosure, and wherein the angle between the first and second panels is at least 30 degrees.

9. The skin illumination device of claim 8, further comprising a sealing rim that is configured to contact epidermis of the subject.

10. The skin illumination device of claim 8, further comprising a suction system that is operable to draw tissue of the subject into the irradiation enclosure.

11. The skin illumination device of claim 1, wherein a plurality of the LEDs forming the matrix of LEDs are configured to generate and project an illumination light, consisting of wavelengths of 850 nm to 1100 nm and wherein wavelengths of the plurality of the LEDs are selected to effectively pass-through epidermis and dermis of the subject.

12. The skin illumination device of claim 1, wherein the near-infrared range of light generated by the LEDs is selected from the group of ranges consisting of: 900 nm to 920 nm, 940 nm to 960 nm and 1010 nm to 1100 nm; and
wherein the generator is a pulsed electromagnetic field generator comprising a coil with a ferromagnetic core for generating the pulsed electromagnetic field.

13. A method for cosmetic treatment of skin of a subject, comprising:
providing a skin illumination device having a panel with a matrix of LEDs configured to generate light in near-infrared range;
applying the panel of the skin illumination device to epidermis of the subject;
operating the skin illumination device to generate light in a near-infrared range with wavelengths selected to penetrate through the epidermis and dermis of the subject;
employing an intensity of the light to penetrate through the epidermis and the dermis to heat adipocytes in a portion of a subcutaneous fat layer of the subject;
concurrently applying a pulsed electromagnetic field to the volume of tissue that includes the subcutaneous fat layer;
wherein the pulsed electromagnetic field has a field strength of not less than 10 Gauss and not more than 30 Gauss and has a magnetic pulse frequency of not less than 0.1 Hz and not more than 100 Hz; and
initiating adipocytes apoptosis and destroying adipocytes.

14. The method for cosmetic treatment of skin of claim 13, wherein the intensity of the light employed causes the light to heat the adipocytes to a temperature of above 42° C.

15. The method for cosmetic treatment of skin of claim 13, further comprising:
concurrently with applying light to a portion of epidermis sufficiently, cooling the illuminated portion of epidermis to prevent burn damage to the epidermis.

16. The method for cosmetic treatment of skin of claim 15, wherein the cooling comprises contacting the portion of epidermis with a cooling surface of a sapphire window having a temperature of 5° C. to 20° C.

17. The method for cosmetic treatment of skin of claim 13, wherein the operating of the skin illumination device to generate light comprises operating a plurality of LEDs forming the matrix of LEDs to generate an illumination light consisting of wavelengths of 850 nm to 1100 nm and having a power density in a range from 0.3 W/cm$^2$ to 5 W/cm$^2$.

18. The method for cosmetic treatment of skin of claim 13, wherein the operating of the skin illumination device comprises generating the illumination light continuously with a duration of at least 10 minutes.

19. A method for cosmetic treatment of a portion of a human body, comprising:
employing an incoherent multi-source and multi-wavelength illumination light for, transdermally heating a portion of a subcutaneous fat layer of a subject and wherein illumination at a surface of epidermis has a cross-sectional area with dimensions of 35 cm$^2$ with a power density of 1.6 W/cm$^2$, the heating sufficient to destroy at least one adipocyte in the portion of the subcutaneous fat layer and to initiate apoptosis thereof;
applying a pulsed electromagnetic field to the volume of tissue that includes the subcutaneous fat layer, the electromagnetic field having a field strength of between 10 Gauss and 30 Gauss and a frequency of between 0.1 Hz and 100 Hz; and
cooling the portion of epidermis sufficiently to prevent burn damage to the epidermis; and
wherein the illumination includes wavelengths in a near-infrared range of 850 nm to 1100 nm.

* * * * *